United States Patent
Yang

(10) Patent No.: US 10,456,233 B2
(45) Date of Patent: Oct. 29, 2019

(54) INTRAVASCULAR FILTER CUT FROM SHEET METAL

(71) Applicant: Cook Medical Technologies LLC, Bloomington, IN (US)

(72) Inventor: Shuo Yang, West Lafayette, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 255 days.

(21) Appl. No.: 15/370,382

(22) Filed: Dec. 6, 2016

(65) Prior Publication Data

US 2017/0172721 A1    Jun. 22, 2017

Related U.S. Application Data

(60) Provisional application No. 62/270,821, filed on Dec. 22, 2015.

(51) Int. Cl.
*A61F 2/01* (2006.01)
*B21D 28/26* (2006.01)

(52) U.S. Cl.
CPC ............. *A61F 2/01* (2013.01); *B21D 28/26* (2013.01); *A61F 2002/016* (2013.01); *A61F 2002/018* (2013.01); *A61F 2210/0014* (2013.01); *A61F 2210/0095* (2013.01); *A61F 2220/0016* (2013.01); *A61F 2230/005* (2013.01); *A61F 2230/0067* (2013.01); *A61F 2230/0086* (2013.01); *A61F 2240/001* (2013.01); *A61F 2250/0039* (2013.01); *A61F 2310/00023* (2013.01)

(58) Field of Classification Search
CPC .......... A61F 2/01; A61F 2002/018; A61F 2210/0095; A61F 2220/0016; A61F 2230/005; A61F 2230/0067; A61F 2240/001; A61F 2250/0039; A61F 2310/00023; A61F 2210/0014; A61F 2002/016; B21D 28/26

See application file for complete search history.

(56) References Cited

U.S. PATENT DOCUMENTS

| | | | |
|---|---|---|---|
| 5,907,893 | A | 6/1999 | Zadno-Azizi et al. |
| 6,152,946 | A | 11/2000 | Broome et al. |
| 6,881,218 | B2 | 4/2005 | Beyer et al. |
| 7,625,399 | B2 | 12/2009 | Case et al. |
| 7,722,635 | B2 | 5/2010 | Beyer et al. |
| 8,231,650 | B2 | 7/2012 | Cully et al. |

(Continued)

FOREIGN PATENT DOCUMENTS

EP    2 626 106 A1    8/2013

OTHER PUBLICATIONS

Extended European Search Report dated Jan. 24, 2017.

*Primary Examiner* — George J Ulsh
(74) *Attorney, Agent, or Firm* — Brinks Gilson & Lione

(57) ABSTRACT

The present disclosure describes filter devices for deployment to body vessels where clots or emboli may need to be captured, particularly the vena cava. The filter device is of unitary construction, having been cut from a substantially planar sheet of a metal, in some instances a shape memory metal. The device has a construction including a plurality of petals, the petals containing an inner rib which curves in the deployed state. A method of making a filter device is also disclosed.

20 Claims, 10 Drawing Sheets

(56) References Cited

U.S. PATENT DOCUMENTS

| | | |
|---|---|---|
| 8,313,503 B2 | 11/2012 | Cully et al. |
| 8,562,624 B2 | 10/2013 | Uihlein |
| 9,060,886 B2 | 6/2015 | Molaei et al. |
| 2002/0026203 A1 | 2/2002 | Bates et al. |
| 2007/0203520 A1* | 8/2007 | Griffin ............... A61F 2/01 606/200 |
| 2008/0039891 A1* | 2/2008 | McGuckin, Jr. ......... A61F 2/01 606/200 |
| 2009/0299404 A1 | 12/2009 | Chanduszko et al. |
| 2010/0030253 A1* | 2/2010 | Harris ............... A61F 2/01 606/200 |
| 2010/0121373 A1 | 5/2010 | Tekulve |
| 2014/0348860 A1 | 11/2014 | Barbick et al. |
| 2015/0150671 A1 | 6/2015 | Gilson et al. |

\* cited by examiner

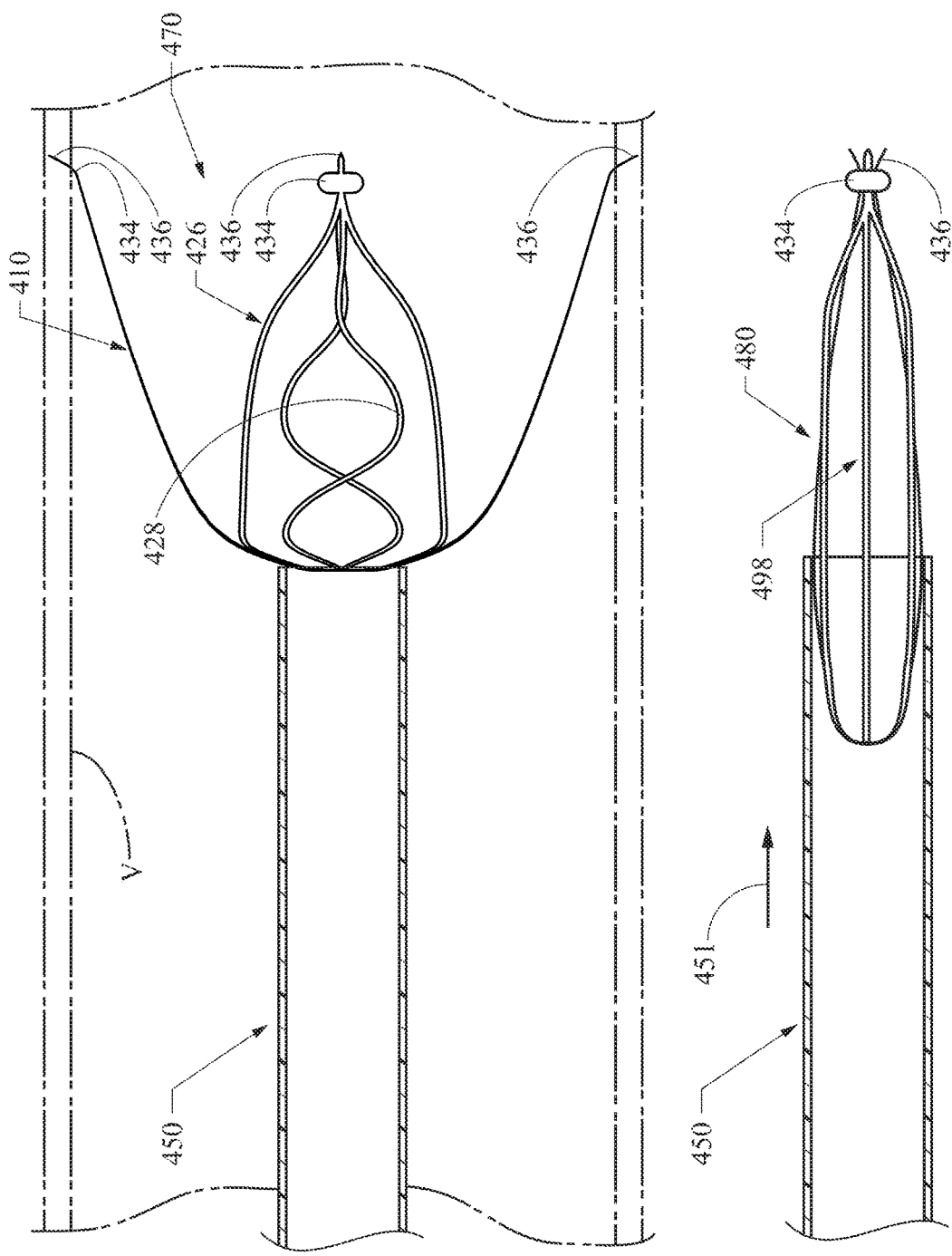

INTRAVASCULAR FILTER CUT FROM SHEET METAL

CROSS-REFERENCE TO RELATED APPLICATIONS

This application claims the benefit of priority under 35 U.S.C. § 119(a) to U.S. Provisional Application No. 62/270,821, filed Dec. 22, 2015 all of which are hereby incorporated by reference in their entirety.

BACKGROUND

The present invention relates to medical devices. More particularly, the invention relates to a vena cava clot filter that can be percutaneously placed in the vena cava of a patient.

A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood clots migrate from the peripheral vasculature through the heart and into the lungs.

A filtering device can be deployed in the vena cava of a patient when, for example, anticoagulant therapy is contraindicated or has failed. Typically, filtering devices are permanent implants, each of which remains implanted in the patient for life, even though the condition or medical problem that required the device has passed. In more recent years, filters have been used or considered in preoperative patients and in patients predisposed to thrombosis which places the patient at risk for pulmonary embolism.

Currently available vena cava filters generally include a number of struts formed from individual pieces of wire arranged to give the filter its shape and collected at one end by a separate piece that gathers the ends of the struts together, such as a collet, a bushing, or a sleeve, generally referred to as a hub. Although these devices are effective, their construction could be simplified.

There is a need for filter devices which are simple to make and provide geometries that are efficacious for capturing emboli and clots.

BRIEF SUMMARY

In one aspect, the present disclosure provides a filter device for implantation into a body vessel, the device having a hub; and a plurality of struts extending radially from the hub, each strut having a first end connected to the hub and extending radially therefrom to a second end, the second ends of two radially adjacent struts being connected at a tip to form a petal having a gap between the radially adjacent struts, each petal comprising an inner rib extending from the hub through the gap to the tip of the petal.

In another aspect, the present disclosure describes a filter device for implantation into a body vessel, the device having a hub which is a center ring. The device also includes a plurality of struts extending radially from the hub, each strut having a first end connected to the hub and extending radially therefrom to a second end, the second ends of two radially adjacent struts being connected at a tip to form a petal having a gap between the radially adjacent struts, each petal comprising an inner rib extending from the hub through the gap to the tip of the petal. The device includes a pad at each petal tip for contacting the wall of the body vessel, each pad comprising a barb for engaging the wall of the body vessel. The filter device is of unitary construction and being cut from a substantially planar piece of a shape memory metal.

In another embodiment, the present disclosure provides a method of making an intravascular filter device. The method includes steps of cutting a substantially planar piece of material to form a filter device, the filter device comprising a hub and a plurality of struts extending radially from the hub, each strut having a first end connected to the hub and extending radially therefrom to a second end, the second ends of two radially adjacent struts being connected at a tip to form a petal having a gap between the radially adjacent struts, each petal comprising an inner rib extending from the hub through the gap to the tip of the petal, the filter device being in a flat configuration; placing the filter device at a distal end of a tubular mandrel having a lumen formed therethrough, the mandrel having a proximal end and extending to the distal end; and pulling the filter device through the distal end in the proximal direction and into the lumen such that the filter device adopts a expanded configuration by contact with the mandrel.

Further objects, features, and advantages of the present invention will become apparent from consideration of the following description and the appended claims when taken in connection with the accompanying drawings.

BRIEF DESCRIPTION OF THE DRAWINGS

The drawings are purely schematic illustrations of various aspects of the invention and are not necessarily to scale, unless expressly stated.

FIG. 8A is a side view of a filter device deployed to a blood vessel and a retrieval sheath;

FIG. 8B is a side view of the filter device of FIG. 8A being pulled into the retrieval sheath.

DETAILED DESCRIPTION

While the present invention has been described in terms of certain preferred embodiments, it will be understood that the invention is not limited to the disclosed embodiments, as those having skill in the art may make various modifications without departing from the scope of the following claims.

The terms "substantially" or "about" used herein includes variations in the recited characteristic or quantity that are functionally equivalent to the quantity recited, such as an amount that is equivalent to the quantity recited for an intended purpose or function. In the case of a numerical quantity, the terms "substantially" or "about" shall mean a range consisting of a value 20% less than the recited value to a value 20% greater than the recited value, inclusive.

As used herein, the terms "upstream" and "downstream" particularly refer to the direction of blood flow through a vessel. Blood flows from upstream to downstream. Reference made to an upstream or downstream end or portion of a filter device is done with reference to the deployed configuration of the device, with blood moving from the upstream end toward the downstream end of the device when the device has been deployed to a blood vessel.

As used herein, the terms "expanded configuration" and "deployed configuration" are to be understood as substantially interchangeable with regard to the shape of a filter device. Typically, the expanded configuration and the deployed configuration are substantially identical; "expanded" being used to describe the device when it has been shaped out of its flat configuration but not necessarily deployed to a body vessel, and "deployed" being used to describe a device which is resident in a blood vessel. A person of skill in the art will recognize that any dissimilarity between the expanded configuration and the deployed configuration will arise from the constraint applied by the wall of the vessel to which the filter device has been deployed.

As used herein, the term "unitary construction" refers to the structural components of a filter device, such as a strut, a hub, a barb, a pad structure, all being formed from the same piece of precursor material, preferably a substantially planar piece of a metal, the metal preferably being a shape memory alloy. Non-structural components, such as coatings, radiopaque markers, and the like, may be added to the device without detracting from the unitary construction of the structure of the device.

Figure 1:
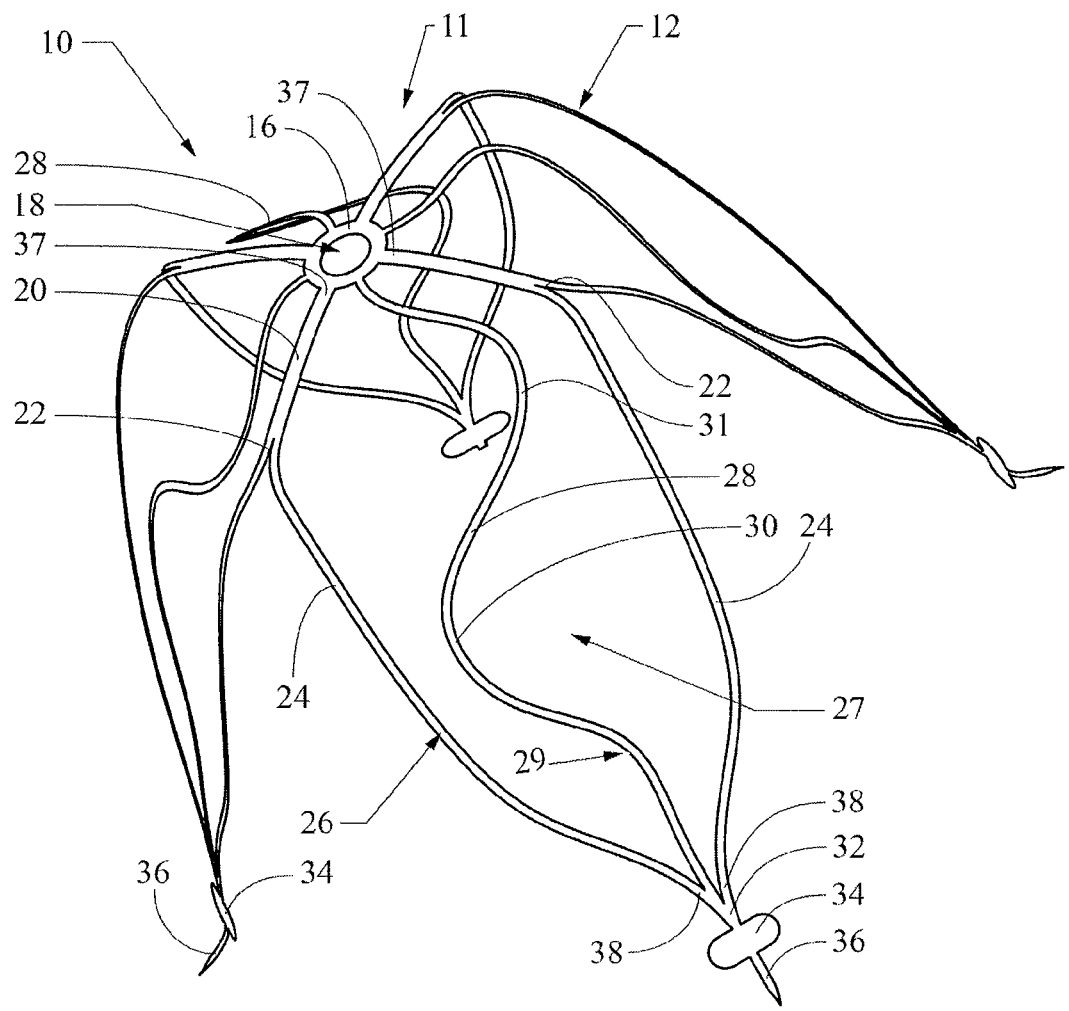
FIG. 1 is a perspective view of a filter in a expanded configuration or deployed configuration in accordance with one embodiment of the present invention.

FIG. 1 illustrates a first embodiment of a filter device 10 in accordance with the principles of the present disclosure. The filter device 10 is shown in its expanded configuration 11 and comprises a plurality of struts 12, which each have a first end 37 attached to a center or hub 16. It should be noted that unlike certain devices already known in the art, the hub 16 is not a separately-formed piece which gathers ends of struts in, for instance, a collet or a sleeve; rather, as used herein, a hub is a portion of a unitary device from which struts generally emanate.

The struts 12 extend from first ends 37, which are connected to the hub 16, radially outward to second ends 38. In one embodiment, the struts 12 comprise first segments 20 and angle at second segments 24. In one embodiment, the first segments 20 of two radially adjacent struts 12 are conjoined, as illustrated in FIG. 1, but first segments 20 may be formed separately from one another as well. In the embodiment of FIG. 1, the first segments 20 disjoin and angle to form second segments 24 at split 22.

Two radially adjacent struts 12 comprise petals 26. The petals 26 each define a gap 27 between the two radially adjacent struts 12, with the second ends 38 of struts 12 converging at tip 32. It is noted that in FIG. 1, the radially adjacent struts 12 that have conjoined first segments 20 form portions of two different petals 26, and the struts 12 which form a single petal 26 are not conjoined at their first segments.

As shown in FIG. 1, the device comprises four petals 26. However, other numbers of petals are possible when the device has radial symmetry, including three petals, five petals, six petals, seven petals, eight petals, nine petals, 10 petals, 11 petals, 12 petals, 14 petals, 16 petals, 18 petals, 20 petals, 22 petals, and 24 petals.

Pad structure 34 is present at tip 32 of petal 26 in the embodiment of FIG. 1. The pad structure is a perforation preventing pad, and is designed to lay flat against the wall of a vessel to which the filter device has been deployed in order to allow the barbs 36 of the device to engage the wall, but not perforate it to such a degree to cause injury. As shown in FIG. 1, the pad structure 34 is shown as oval or elliptical in shape, but any polygonal or ring shape can be employed so long as the function of the pad 34 is retained.

Barb 36 of device 10 of FIG. 1 is located downstream of pad structure 34. The barbs 36 of this disclosure will be described in detail with regard to FIGS. 5A-C. The function of the barbs 36 is to engage the wall of the vessel in order to prevent migration of the device.

The inner rib 28 is located in gap 27 of petal 26. The inner rib 28 extends from hub 16 to tip 32, and comprises curves with peaks 29, 30, and 31, which gives the inner rib 28 a greater overall length than the struts 12.

The inner rib 28 provides the filter device 10 with a number of abilities. Foremost, each inner rib 28 adds a solid portion within each petal 26, providing more connections to hub 16 and thus providing the filter device 10 with more surface area on which to catch smaller clots or emboli. The inner rib 28, because of its curved nature, also serves to accommodate foreshortening when the filter device 10 is put into its compressed configuration and loaded into a delivery system. The curvature of the inner rib 28 provides sufficient slack for packaging of the device 10, but is not so long as to increase the profile of the device in the compressed configuration. As will be shown later, inner rib 28 straightens when the device is in its compressed form in the delivery device.

The inner rib 28 may be of a number of designs. In one embodiment, it is sinuous and curved but does not have three peaks. The inner rib 28 may be of any configuration as long as the length of inner rib 28 is greater than or equal to the length of the petal 26 in which it resides when the device is in its compressed configuration.

The inner rib 28 reinforces the filter device 10 and provides additional radial force against the wall of a vessel to which the filter device 10 has been deployed. As a result, filter apposition is improved, and the chances of migration of the filter are minimized. Further, the inner rib 28 may serve as a redundant structure; should a strut of the petal 26 in which the inner rib 28 resides fail for any reason, the filter device 10 should still function and remain in place, and will still be retrievable.

The hub 16, as shown in FIG. 1, is a ring with empty center 18. Alternate designs are possible and will be described later. An empty center 18 will be accommodating of retrievability, such that a retrieval assembly with an element such as a hook will be able to engage the center and snare the filter device 10 so as to more surely guarantee retrieval.

In another embodiment, the empty center 18 may be provided such that a retrieval member may be attached to the device after assembly of the filter device 10. Such a retrieval member may be, for instance, a hook that can be fit through the empty center 18 and welded or soldered into place. This would allow for simplified grasping by a retrieval snare.

Figure 2:
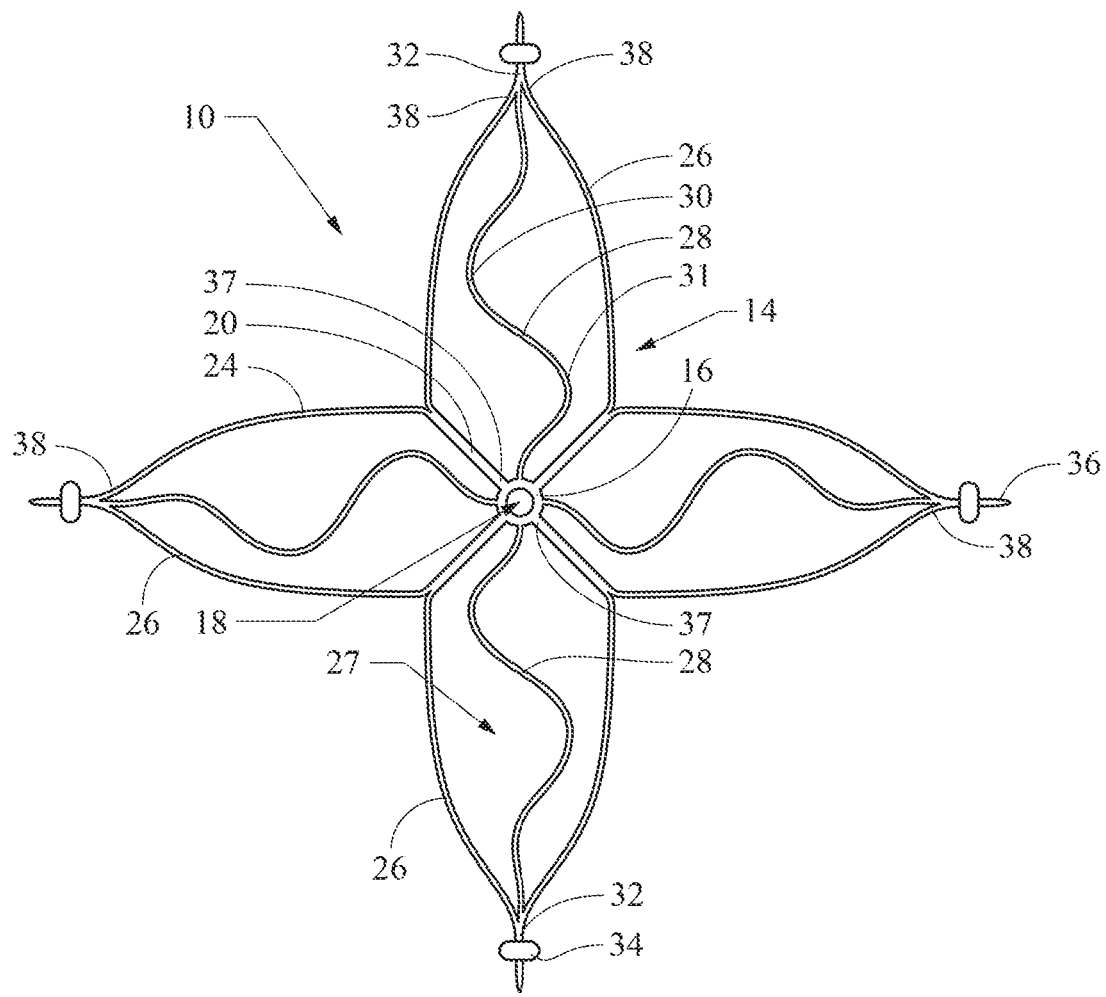
FIG. 2 is a view of the filter device of FIG. 1 in its flat configuration in accordance with the principles of the present disclosure.
Figure 3:
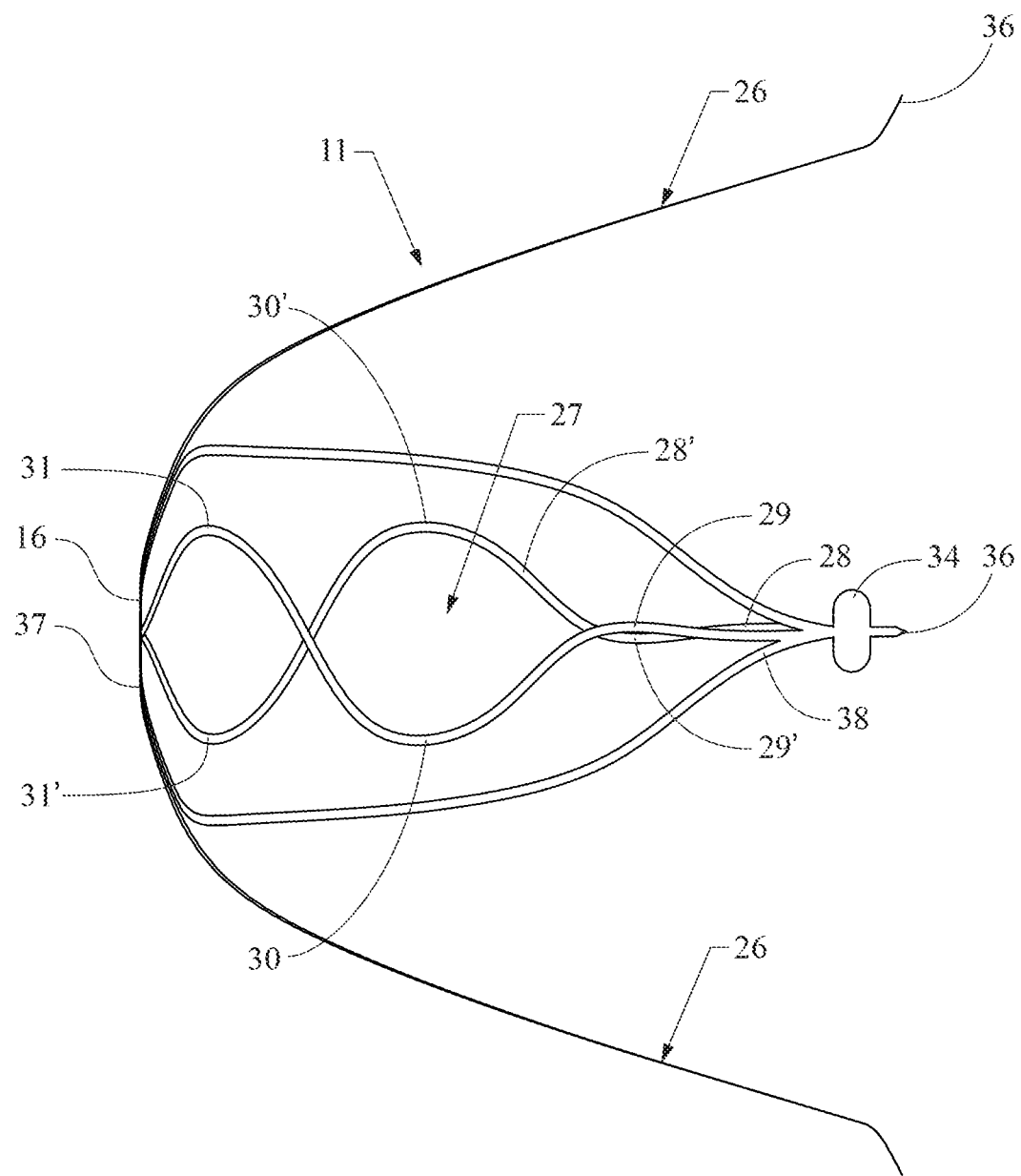
FIG. 3 is a side view of the filter device of FIGS. 1 and 2 in its expanded or deployed configuration.

FIG. 2 illustrates the flat configuration 14 of device 10 of FIG. 1. In this illustration, the four petals 26 and the overall radial symmetry of the device can be seen. The peaks 30,31 of the curved inner rib are present, showing their residence in gap 27 of the petals 26. Overall, cutting from a sheet of metal rather than a cannula results in the ability to create more complex geometries such as the central hub 16, the inner rib 28, and the perforation preventing plates 34. FIG. 3 provides a side view of the device 10 of FIGS. 1 and 2 in expanded configuration 11.

In one embodiment, a self-expanding intravascular filter in accordance with the principles of the present disclosure can be made of a shape memory material. One example of a shape memory material is a shape memory metal, in particular a class of nickel-titanium alloys, including those marketed under the name NITINOL. Such alloys are known for their shape memory and pseudoelastic properties. As a shape memory material, such a nickel-titanium alloy is able to undergo a reversible thermoelastic transformation between certain metallurgical phases. A device made from a shape memory material, in some embodiments a nickel-titanium alloy, can be heat set to retain its shape after implantation.

In another embodiment, a filter device may be made of a stainless steel, such as stainless steel 304.

The device is particularly envisioned to be of unitary construction. In one sense, a device of unitary construction is made of a single piece of precursor material, such as a substantially planar sheet of metal. Specifically, a sheet of a shape-memory metal such as a nickel-titanium alloy may be laser-cut to yield the filter device. Unitary construction and laser cutting allows for the use of a single pattern to generate the device without the complications and possibilities for introduction of error that derive from weaving, soldering, or using another method to connect separate parts into a unit. As used herein, the term "unitary" means that the device is made of a single piece which has not been joined to another piece.

Figure 4:
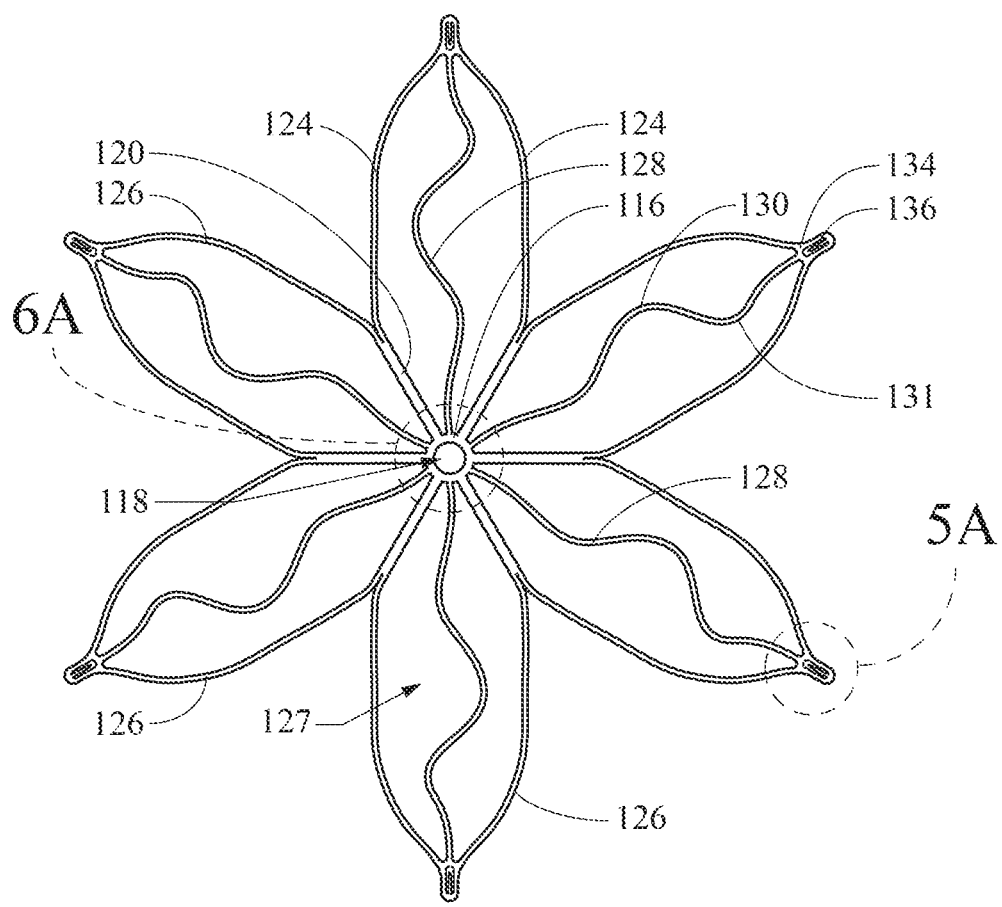
FIG. 4 is a view of a second embodiment of a filter device in its flat configuration in accordance with the principles of the present disclosure.

Turning now to FIG. 4, an alternative embodiment of a filter device in accordance with the principles of the present disclosure is attached. Numerous aspects of the device can be altered and fall within the principles of the invention. Regarding FIG. 4, device 110 has six petals 126 radially surrounding the hub 116, and the barbs 136 are configured differently than the device of FIGS. 1-3.

Figure 5A:
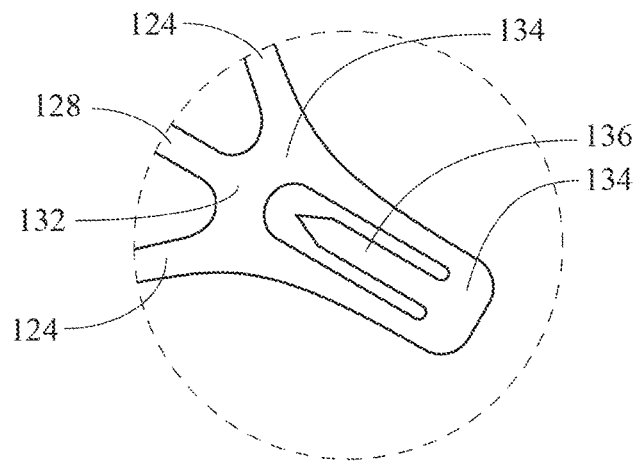
FIGS. 5A-5C are closeup views of barbs formed for a filter device in accordance with the principles of the present disclosure.
Figure 5B:
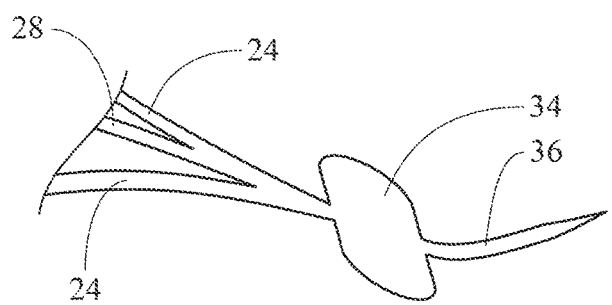
Figure 5C:
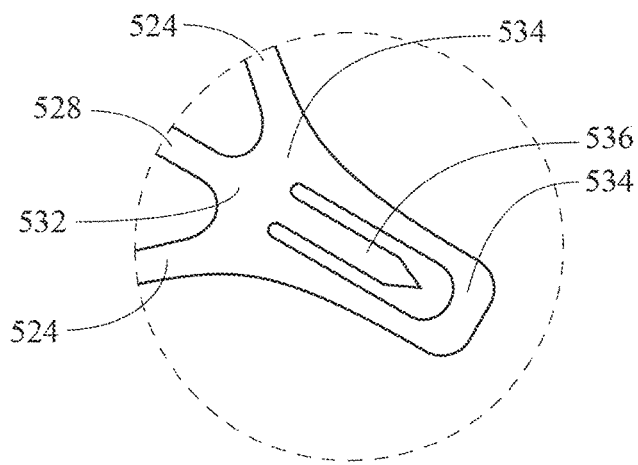

To further support the anchoring of the filter device to the vessel, hooks or barbs may be incorporated onto the outer surface of the device. FIG. 5A-C illustrate a number of barbs which will permit anchoring of a device to a vessel wall. In a preferred embodiment these barbs may be cut from the structure and bent outward.

FIG. 5B illustrates barbs in accordance with embodiment shown in FIGS. 1-3. Here, the barb 36 is bent out of the plane of the rest of the device 10 and lies upstream of the pad structure 34.

FIGS. 5A and 5C show barb configurations in which the barb is cut from a space within the pad structure. The barb 136 of FIG. 5A is formed from within pad structure 134 and points with its point in the downstream direction, whereas barb 536 of FIG. 5C is formed within pad structure 534 but points with its point in the upstream direction. In either case, the barb 136/536 will be bent out of the plane of the pad 134/534 in order that the barbs 136/536 can engage the wall of a vessel V into which the device 110/510 is implanted.

Barbs may face the upstream direction, which will not interfere with retrieval. However, if a more secure hold is desired and the barbs are designed to be bent back such that their pointed ends point back in the downstream direction, the filter device, and particularly the petals, need to have a concave geometry so that retrieval can proceed as shown in FIG. 8B.

It is intended that any of the barb configurations shown in FIGS. 5A-5C can be combined with any other design of the filter device and still fall within the scope of the present invention. In one embodiment, the barb configurations may vary on a petal-to-petal basis; that is, one petal may have a barb as in FIG. 5B, and the radially adjacent petal may include a barb as in FIG. 5A.

Figure 6A:
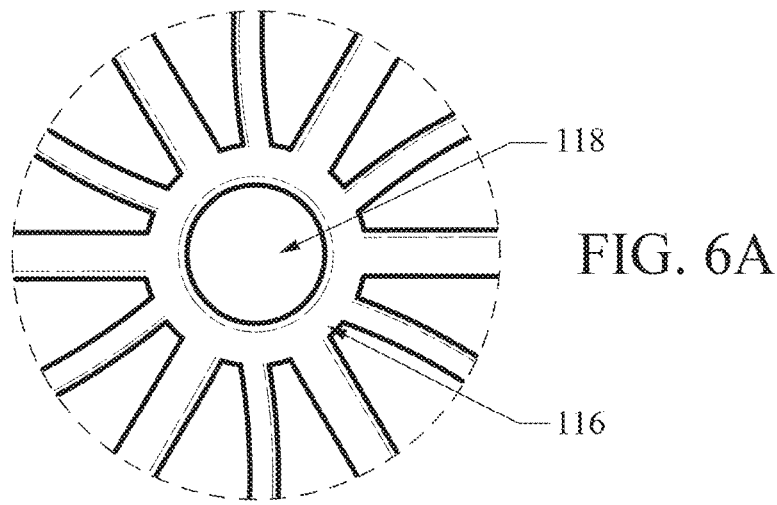
FIGS. 6A-6C are closeup views of centers of various embodiments of filter devices in their flat configurations and which are constructed in accordance with an embodiment of the present disclosure.
Figure 6B:
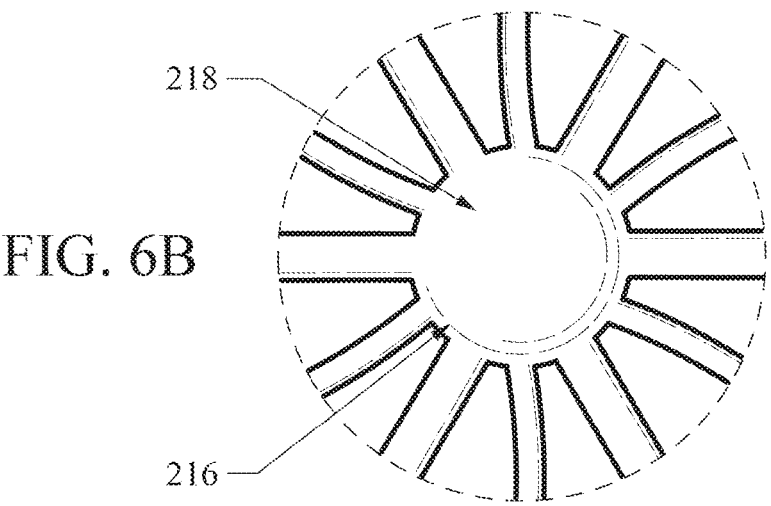
Figure 6C:
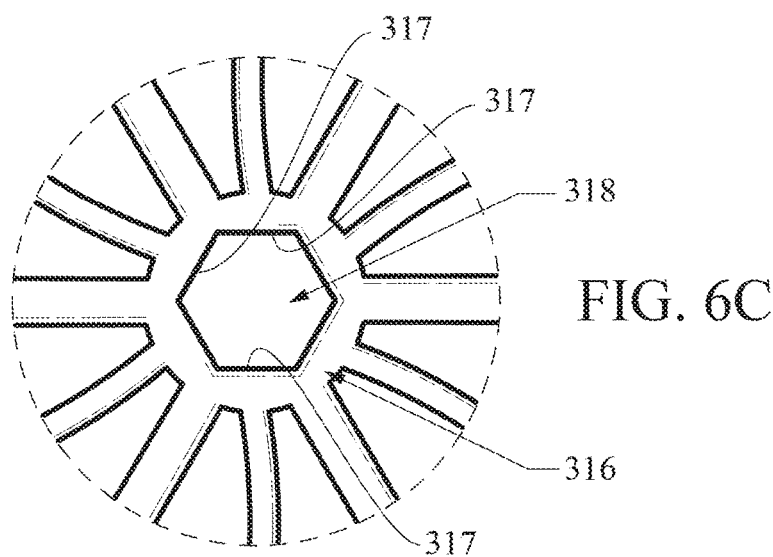

FIG. 6A-C illustrate various structures that can be used at hubs. Hub 116 is similar to the hubs shown in the embodiments of FIGS. 1-4, wherein the hub is a ring shape with an aperture 118 formed therethrough. As mentioned previously, this open aperture 118 may aid in simplifying retrieval of the filter device from a vessel to which it has been deployed, as a retrieval member such as a hook or a snare can be fed therethrough. The embodiment of FIG. 6C is similar, with the hub 316 having a polygonal shape, in this case a hexagonal aperture 318 with edges 317 is formed therethrough.

FIG. 6B shows a device having hub 216, which is a closed circle 218. Such a hub configuration may be preferred for an embodiment of a filter device which is not to be retrieved, and the closed end may assist in increasing the capacity of the filter to capture clots or emboli. However, a snare which targets a different portion of the filter device could be used, and therefore a device having hub 216 with closed circle 218 could still be a retrievable filter.

The outer diameter of the hub 16/116/216/316 may be limited by the size of the sheath of the delivery system. In various embodiments, diameter of the hub may range from about 7 french to about 15 french, or from about 2.5 millimeters to about 5 millimeters.

Figure 7A:
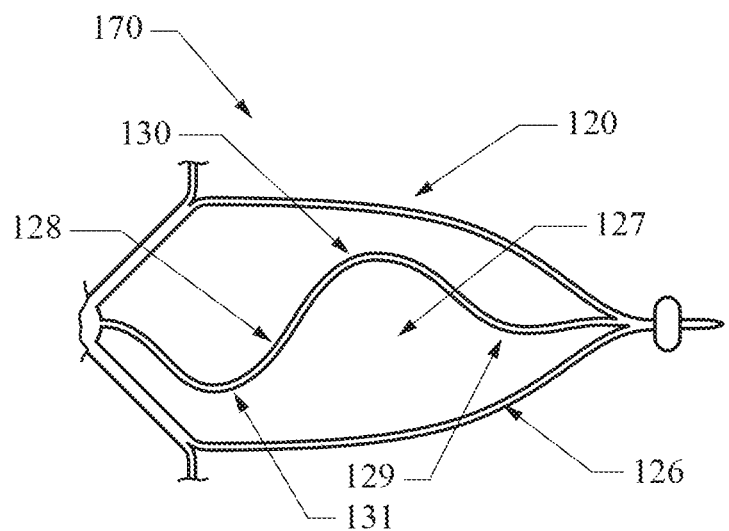
FIG. 7A is a side view of a petal of a filter device in its deployed configuration in accordance with an embodiment of the present disclosure.

Turning now to FIG. 7A, a petal 126 in accordance with one embodiment of the present disclosure is illustrated. The petal is part of a device in a deployed configuration or an expanded configuration 170. When the device is in this configuration, the struts take on arcuate shape 120, and inner rib 128 takes on a sinuous shape, the inner rib 128 being curved such that curve peaks 129, 130, and 131 are evident. As mentioned previously, the curved rib increases clot capture area, increase radial force produced, strengthens the device, acts as a redundant feature in case of failure of a strut, and accommodates foreshortening.

Figure 7B:
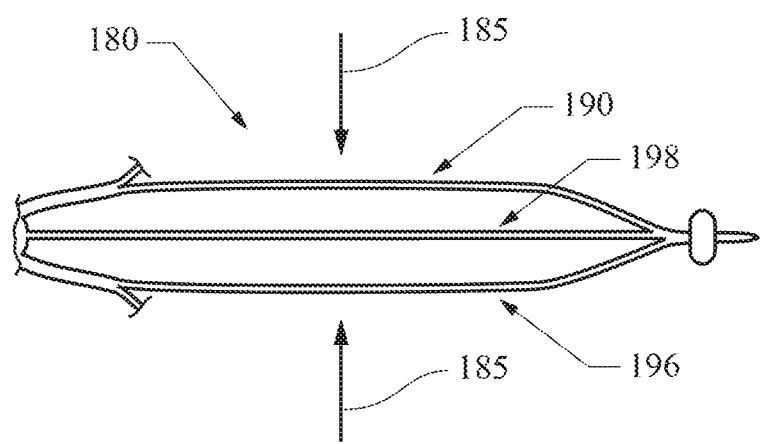
FIG. 7B is a side view of the petal of FIG. 7A in its compressed configuration.

In contrast, FIG. 7B shows the petal of FIG. 7A is shown in its compressed configuration 180 and is referred to as compressed petal 196. As mentioned previously, the typical situation in which a device of this construction will be in its compressed configuration is when the device is packed into and loaded in a delivery apparatus prior to delivery into the vasculature of a patient. In this configuration, compressive force 185 as applied to the device, and the struts take on straightened shape 190. Notable is the straightening of the inner rib 128 to substantially straight configuration 198. In some cases, such as that illustrated, the straightening may be so extensive that the peaks of any curve may no longer be evident.

With regard to retrieval of the device, FIG. 8A shows deployed device 410 in a blood vessel. Barbs 436 engage the wall of vessel V, and pad structures 434 prevent the barbs 436 from puncturing the vessel wall. Because the device is in deployed configuration 470, the inner rib 428 is sinuous in shape.

In FIG. 8B, retrieval sheath 450 has moved in direction 451 to capture the filter 410. Not shown is an optional retrieval member, such as a hook, for engaging the hub. The concave profile of the filter device 410, particularly owing to the shapes of petals 426, increases retrievability. During retrieval, the inner rib straightens to straight configuration 498, and the barbs 436 move toward the axial center of vessel V. This minimizes or prevents contact between the barbs 436 and the retrieval sheath 450, such that the points of the barbs do not damage the retrieval sheath 450. In some embodiments, the barbs 436 may move through and past the longitudinal axis of the vessel V. Any variety of device configurations which avoid contact between the barbs 436 and the retrieval sheath are possible.

The device may, optionally, further incorporate radiopaque markers to assist a physician with placement in the body. Many suitable radiopaque materials are known and any of these may be selected for use with a device of the present disclosure. The radiopaque markers may be made of materials including gold, palladium, tantalum, platinum, and biocompatible alloys of any of these materials.

Further, a device as disclosed herein may be used with many existing delivery systems as are known in the art. Particularly when a device is made of a shape memory metal such as a nickel-titanium alloy, the final dimensions of the device are determined by the remembered state and not dependent upon manipulating the delivery system to crimp or otherwise modify the device as it is being loaded.

Many possible variations on a device of this construction are also possible. If desired, the filter device may be covered with a porous or non-porous layer which has drug-eluting properties. All coatings or biological coverings may be attached by any known method, including spray coating and the like.

A device in accordance with the principles of the present disclosure may be made according to a series of steps, as illustrated in FIGS. 9A-9D. As mentioned previously, a single, monolithic, sheet of a shape memory alloy may be precisely laser cut to generate the overall shape of the filter device.

Figure 9A:
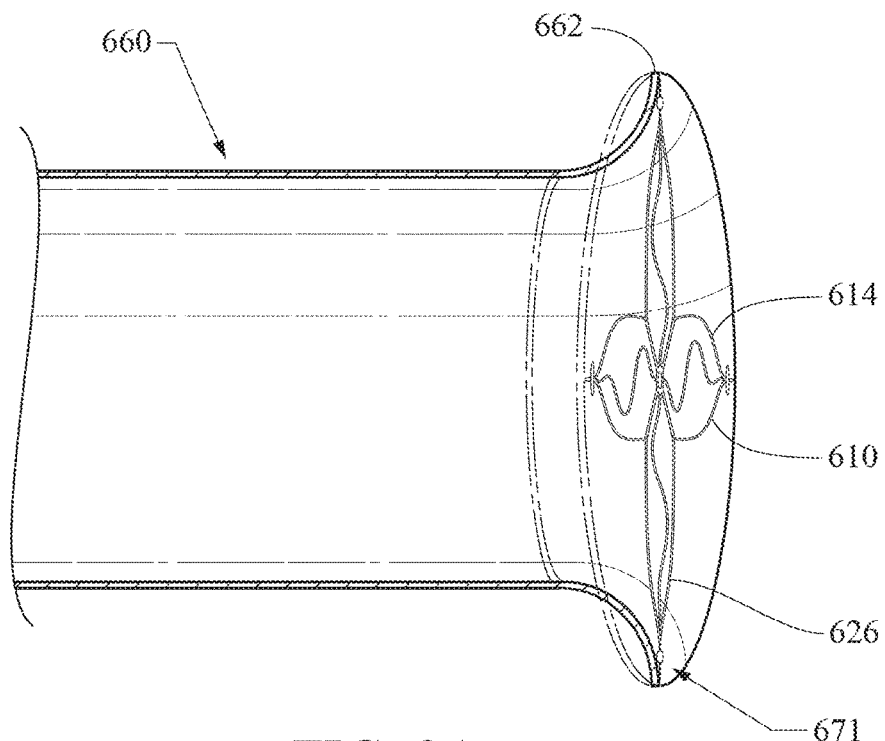
FIGS. 9A-9D are side views of a filter device constructed in accordance with the principles of the present invention being converted from its flat configuration to its expanded configuration using a tubular mandrel in accordance with the principles of the present disclosure.
Figure 9B:
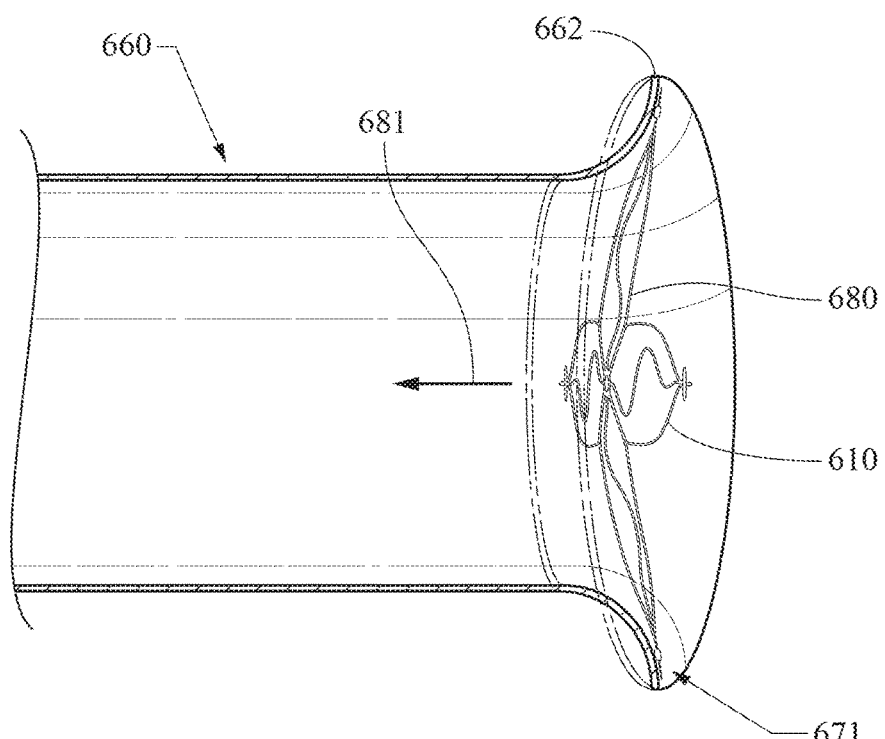
Figure 9C:
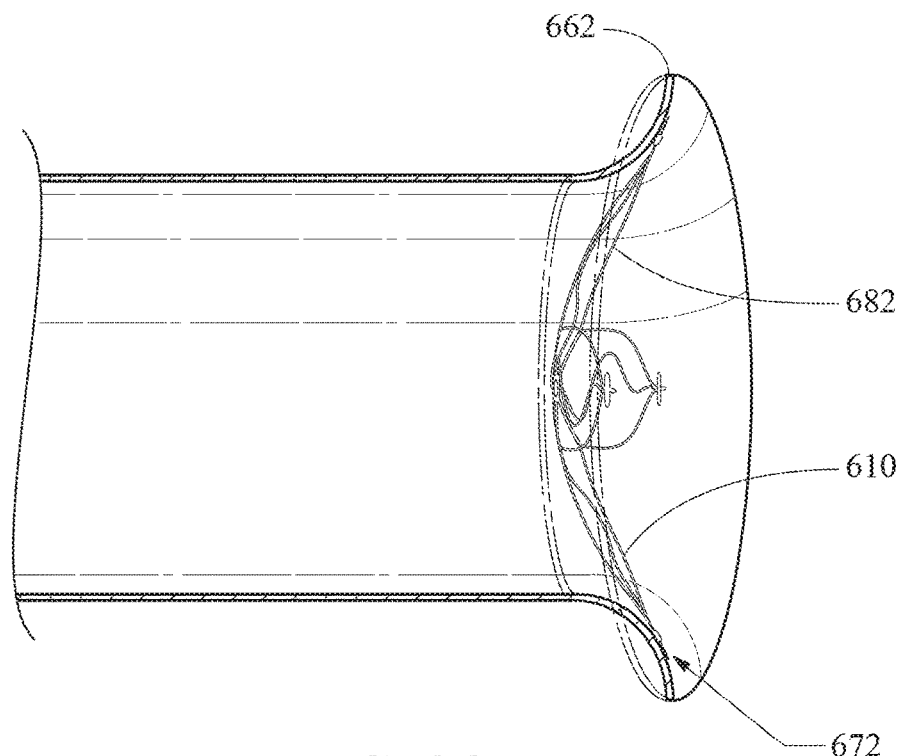
Figure 9D:
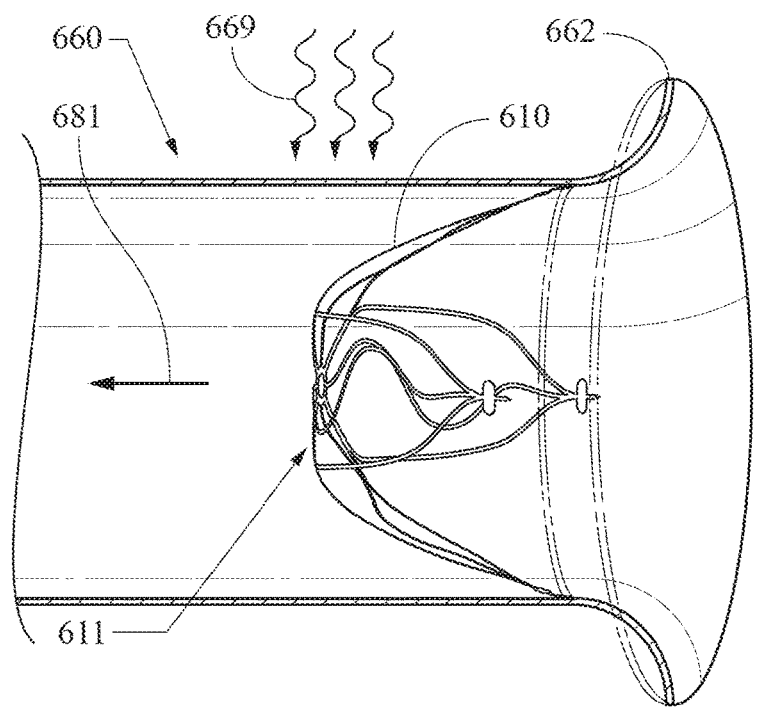

In FIG. 9A, a device 610 in its flat configuration 614 has been placed at a distal end 626 of a substantially tubular mandrel 660. The device 610 makes contact at the open end of the tubular mandrel 660 at points of contact 671. In FIG. 9B, the device 610 has been drawn partially into the lumen of the tubular mandrel 660 by pulling in a direction 681 to form partially expanded configuration 680. FIG. 9C illustrates the continued effect of the pulling force in direction 681, which converts the device to partially expanded configuration 682. Finally, in FIG. 9D, the device has achieved expanded configuration 611 due to the continued action of pulling force in direction 681. Optionally, and particularly when a shape memory alloy is used for the device, the device may be heat set by providing heat 669.

The mandrel 660 may be a simple tubular structure, or it may be of a custom shape in order to achieve specific shapes of the device 610. For example, the mandrel 660 of FIGS. 9A-9D is illustrated with a flared end 662 to give the mandrel 660 an overall trumpet-like shape. Many other configurations are possible, including frusto-conical mandrels, and so forth.

In some embodiments, shaping or bending the filter into its expanded configuration may include passing the filter device through a plurality of mandrels.

A method of using a filter device as described in the instant disclosure can include a number of different steps. In one step, the filter device may be compressed to a compressed state and loaded into a delivery assembly. The delivery assembly may be introduced to the body percutaneously, and the device delivered, such as by a pusher, into the lumen of the body vessel, in one embodiment the vena cava, more particularly the inferior vena cava. The filter device, upon deployment, will anchor against the vessel wall as it is deployed from the delivery assembly as it returns to its remembered, unconstrained state. For instance, in the illustration of the filter device deployed to a body vessel of FIG. 8A, the device after removal from the delivery assembly has returned to its unconstrained remembered state, leading to an expansion at the upstream, open end of the filter 410, with the barbs 436 engaging the vessel wall to secure the device within the vasculature. Delivery may be guided by imaging which may optionally include monitoring of one or more radiopaque portions included on the device. After the device has been secured within the body vessel, the delivery assembly is removed from the patient.

While the present invention has been described in terms of certain preferred embodiments, it will be understood that the invention is not limited to the disclosed embodiments, as those having skill in the art may make various modifications without departing from the scope of the following claims.

The invention claimed is:

1. A filter device for implantation into a body vessel, the filter device extending from a proximal end to a distal end and comprising:
   a hub having a proximal face and a distal face; and
   a plurality of struts extending radially from the proximal face of the hub, each strut having a first end connected to the hub and extending radially therefrom to a second end, the second ends of two circumferentially adjacent struts being connected at a tip to form a petal having a gap between the circumferentially adjacent struts, each petal comprising an inner rib extending from the hub through the gap to the tip of the petal.

2. The filter device according to claim 1 wherein the filter device is of unitary construction.

3. The filter device according to claim 1 wherein the filter device comprises a shape memory material.

4. The filter device according to claim 3 wherein the shape memory material comprises a nickel-titanium alloy.

5. The filter device according to claim 1 comprising a barb at each tip.

6. The filter device according to claim 1 further comprising a pad structure adjacent a tip of a petal.

7. The filter device according to claim 6 comprising a barb, the barb being formed by a plurality of cuts of the pad structure.

8. The filter device according to claim 1 having a deployed state and a compressed state, the inner rib comprising a curve in the deployed state and being substantially straight in the compressed state.

9. The filter device according to claim 1 wherein the struts have an arcuate shape.

10. The filter device according to claim 1 wherein the hub is a ring.

11. The filter device according to claim 1 wherein the hub is a solid circle.

12. The filter device according to claim 1 wherein each strut comprises a first segment extending from the first end away from the hub, each first segment being conjoined with a circumferentially adjacent first segment.

13. The filter device according to claim 12 wherein the first segments that are conjoined are portions of two petals.

14. A filter device for implantation into a body vessel, the filter device extending from a proximal end to a distal end and comprising:
   a hub having a proximal face and a distal face and comprising a center ring;
   a plurality of struts extending radially from the proximal face of the hub, each strut having a first end connected to the hub and extending radially therefrom to a second end, the second ends of two circumferentially adjacent struts being connected at a tip to form a petal having a gap between the circumferentially adjacent struts, each petal comprising an inner rib extending from the hub through the gap to the tip of the petal; and
   a pad at each petal tip for contacting the wall of the body vessel, each pad comprising a barb for engaging the wall of the body vessel;
   the filter device being of unitary construction and being cut from a substantially planar piece of a shape memory metal.

15. A method of forming a filter device for implantation into a body vessel, the method comprising:
   cutting a substantially planar piece of material to form the filter device, the filter device extending from a proximal end to a distal end, the filter device comprising a hub, the hub having a proximal face and a distal face; and a plurality of struts extending radially from the proximal face of the hub, each strut having a first end connected to the hub and extending radially therefrom to a second end, the second ends of two circumferentially adjacent struts being connected at a tip to form a petal having a gap between the circumferentially adjacent struts, each petal comprising an inner rib extending from the hub through the gap to the tip of the petal, the filter device being in a planar configuration; and
   bending the filter device to form an expanded configuration.

16. The method according to claim 15 wherein bending the filter device comprises placing the filter device in a planar configuration at a distal end of a tubular mandrel having a lumen formed therethrough, the mandrel having a proximal end and extending to the distal end; and
   moving the filter device through the distal end into the lumen and toward the proximal end such that the filter device adopts the expanded configuration by contact with the mandrel.

17. The method according to claim 16 wherein the filter device is moved through a plurality of mandrels.

18. The method according to claim 16 further comprising a heat setting step.

19. The method according to claim 15 further comprising cutting a barb in the filter device.

20. The method according to claim 19 comprising a step of bending the barb outward.

* * * * *